United States Patent
Alakkat

(10) Patent No.: US 7,125,167 B2
(45) Date of Patent: *Oct. 24, 2006

(54) METHOD AND APPARATUS FOR TILTING IN A PATIENT POSITIONING SYSTEM

(75) Inventor: Shaji Alakkat, Karnataka (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/379,124

(22) Filed: Mar. 4, 2003

(65) Prior Publication Data

US 2004/0172758 A1  Sep. 9, 2004

(51) Int. Cl.
*A61B 6/04* (2006.01)

(52) U.S. Cl. ................. 378/209; 5/601; 5/610

(58) Field of Classification Search ............ 5/600, 5/610, 611, 608, 601; 600/415; 378/208, 378/209

See application file for complete search history.

(56) References Cited

U.S. PATENT DOCUMENTS

| | | | |
|---|---|---|---|
| 1,118,851 A | | 11/1914 | Turner |
| 1,444,042 A | | 2/1923 | Schwalbach |
| 1,952,392 A | * | 3/1934 | Taylor .............. 198/592 |
| 2,091,014 A | * | 8/1937 | Saak ............... 5/610 |
| 2,958,873 A | * | 11/1960 | Ferneau ............ 296/20 |
| 3,588,500 A | | 6/1971 | Koemer |
| 3,868,103 A | * | 2/1975 | Pageot et al. ........ 5/614 |
| 3,944,204 A | | 3/1976 | Cesar |
| 4,013,019 A | | 3/1977 | Horsey |
| 4,071,222 A | | 1/1978 | Wright |
| 4,435,862 A | | 3/1984 | King et al. |
| 4,452,439 A | * | 6/1984 | Hogan ............. 5/601 |
| 4,475,072 A | | 10/1984 | Schwehr et al. |
| 4,484,571 A | | 11/1984 | Velazquez |
| 4,534,076 A | * | 8/1985 | Barge ............. 5/601 |
| 4,541,108 A | | 9/1985 | Grady et al. |
| 4,597,119 A | | 7/1986 | Padgett |
| 4,660,817 A | * | 4/1987 | Kowalski .......... 5/610 |
| 4,715,591 A | | 12/1987 | Dragmen |
| 4,731,889 A | | 3/1988 | Ishikawa |
| 4,751,754 A | | 6/1988 | Bailey et al. |
| 4,761,000 A | * | 8/1988 | Fisher et al. ........ 5/601 |
| 4,767,148 A | * | 8/1988 | Ferneau et al. ...... 296/20 |
| 4,769,584 A | | 9/1988 | Irigoyen et al. |

(Continued)

FOREIGN PATENT DOCUMENTS

DE  268 555 B1  10/1986

(Continued)

*Primary Examiner*—Michael Safavi
(74) *Attorney, Agent, or Firm*—McAndrews, Held & Malloy, Ltd.; Peter J. Vogel; Michael A. Dellapenna

(57) ABSTRACT

Certain embodiments include a system and method for tilting in a patient positioning system. The system includes a tilt plate for tilting a patient positioning surface, a screw for moving the tilt plate, a nut for translating rotary motion into linear motion to drive the screw, and a motor for imparting rotary motion to the nut. In an embodiment, the screw is a ball screw. In an embodiment, the nut is a rotary nut. The system may also include a drive gear situated on the motor, a driven gear situated on the nut the meshes with the drive gear, and a brake gear that meshes with the driven gear. The system may also include a fail-safe brake preventing collapse of the tilt mechanism in the event of a component failure.

13 Claims, 7 Drawing Sheets

U.S. PATENT DOCUMENTS

| | | | |
|---|---|---|---|
| 4,771,785 A | 9/1988 | Duer | |
| 4,841,585 A | 6/1989 | Masuzawa | |
| 4,908,844 A | 3/1990 | Hasegawa | |
| 4,912,754 A | 3/1990 | Van Steenburg | |
| 4,944,500 A | 7/1990 | Mueller et al. | |
| 5,013,018 A | 5/1991 | Sicek et al. | |
| 5,014,292 A | 5/1991 | Siczek et al. | |
| 5,048,071 A | 9/1991 | Van Steenburg | |
| 5,131,105 A * | 7/1992 | Harrawood et al. | 5/607 |
| 5,156,166 A | 10/1992 | Sebring | |
| 5,205,004 A | 4/1993 | Hayes et al. | |
| 5,210,893 A | 5/1993 | Uosaki et al. | |
| 5,237,600 A | 8/1993 | Kamata | |
| 5,272,776 A | 12/1993 | Kitamura | |
| 5,398,356 A | 3/1995 | Pfleger | |
| 5,448,612 A * | 9/1995 | Kasumi et al. | 378/84 |
| 5,473,784 A * | 12/1995 | Nixon et al. | 5/625 |
| 5,572,569 A * | 11/1996 | Benoit et al. | 378/209 |
| 5,575,026 A * | 11/1996 | Way et al. | 5/611 |
| 5,590,429 A * | 1/1997 | Boomgaarden et al. | 5/600 |
| 5,596,779 A | 1/1997 | Meek | |
| 5,659,909 A | 8/1997 | Pfeuffer et al. | |
| 5,826,286 A * | 10/1998 | Cranston | 5/610 |
| 6,038,718 A * | 3/2000 | Pennington et al. | 5/618 |
| 6,094,760 A * | 8/2000 | Nonaka et al. | 5/601 |
| 6,192,585 B1 * | 2/2001 | Buchanan et al. | 29/898.06 |
| 6,195,578 B1 * | 2/2001 | Distler et al. | 600/415 |
| 6,202,230 B1 * | 3/2001 | Borders | 5/618 |
| 6,240,582 B1 | 6/2001 | Reinke | |
| 6,249,695 B1 | 6/2001 | Damadian | |
| 6,269,499 B1 | 8/2001 | Amir | |
| 6,334,708 B1 | 1/2002 | Kosugi | |
| 6,353,949 B1 * | 3/2002 | Falbo | 5/610 |
| 6,456,075 B1 * | 9/2002 | Damadian et al. | 600/415 |
| 6,470,519 B1 | 10/2002 | Pattee et al. | |
| 6,541,973 B1 | 4/2003 | Danby et al. | |
| 6,566,833 B1 | 5/2003 | Bartlett | |
| 6,615,428 B1 | 9/2003 | Pattee | |
| 6,615,429 B1 | 9/2003 | Weil et al. | |
| 6,651,279 B1 | 11/2003 | Muthuvelan | |
| 6,769,145 B1 | 8/2004 | Pfeuffer et al. | |
| 6,769,806 B1 | 8/2004 | Moyers | |
| 6,857,147 B1 | 2/2005 | Somasundaram | |
| 6,934,574 B1 * | 8/2005 | Damadian et al. | 600/415 |
| 2002/0029419 A1 | 3/2002 | Well et al. | |
| 2002/0120986 A1 | 9/2002 | Erbel et al. | |
| 2003/0053599 A1 | 3/2003 | Meyer et al. | |
| 2003/0145383 A1 | 8/2003 | Schwaegerle | |
| 2004/0028188 A1 | 2/2004 | Amann et al. | |
| 2004/0098804 A1 | 5/2004 | Varadharajulu et al. | |
| 2004/0139545 A1 | 7/2004 | Reinke et al. | |
| 2004/0172756 A1 | 9/2004 | Somasundaram | |
| 2004/0172757 A1 | 9/2004 | Somasundaram | |
| 2004/0172758 A1 | 9/2004 | Alakkat | |

FOREIGN PATENT DOCUMENTS

EP        119910        9/1984

* cited by examiner

Up-Down & Rotation (Patient Loading)

Longitudinal Travel (Scanning)

Longitudinal Tilt (Vascular Tilt)

Longitudinal Axis

Head Up tilt (Positive)

Head Down tilt (Negative)

Highest Position

Lowest Position

Fwd. Tilt Position

Reverse Tilt Position

HEAD - DOWN TILT

HEAD - UP TILT

ISO-CENTER TRACKING

Forward tilt (head down)

Forward tilt (head down)

Reverse tilt (head up)

Reverse tilt (head up)

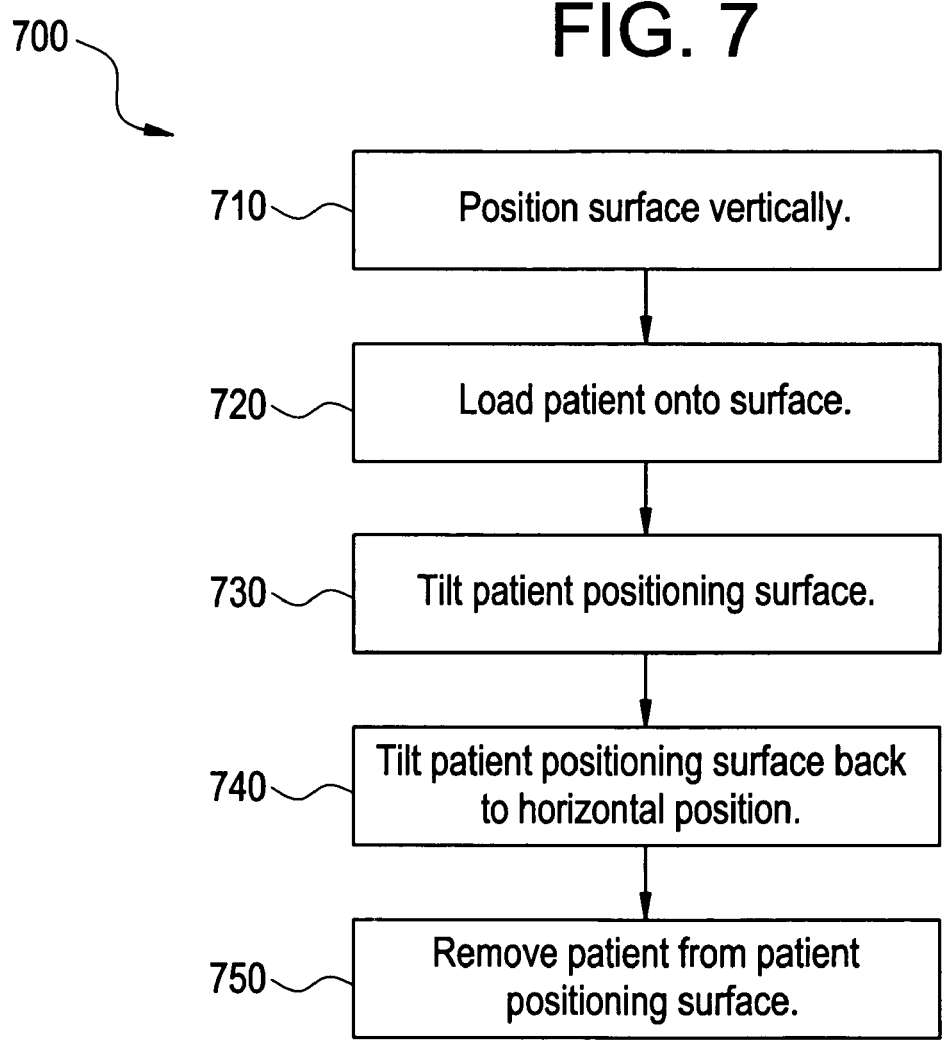

METHOD AND APPARATUS FOR TILTING IN A PATIENT POSITIONING SYSTEM

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to tilting in a patient positioning system. In particular, the present invention relates to a heavy duty tilt mechanism for a patient positioning system.

Patient positioning platforms allow a medical practitioner, such as a doctor, nurse or technician, to position a patient during a medical procedure, such as XR, CT, EBT, nuclear, and PET procedures. Patient positioning platforms, such as tables or other supports, allow a patient to be elevated, moved in lateral and longitudinal directions, rotated and/or tilted during a procedure. Patient positioning platforms improve a medical practitioner's ability to examine and/or perform a medical procedure on a patient.

There is a need for an improved patient positioning platform that may be used in angiography, neurology, and cardiac procedures. Current patient positioner platforms may introduce limitations in obtaining images of blood flow in arteries, heart, lungs, or brain, for example. Thus, a patient positioning system that improves stability and reliable positioning for blood flow imaging in angiography, neurology, cardiac and other such procedures would be highly desirable. Additionally, a patient positioning system that provides reliable and easy positioning of a patient with flexibility to accommodate a variety of medical procedures and emergencies would be highly desirable.

An improved patient positioning platform is capable of tilting a patient to position the patient for a medical procedure. A heavy load may be applied to a patient positioning platform during tilt. Thus, a heavy moment load may be placed on a tilt mechanism of a patient positioning platform. Therefore, a patient positioning platform with an improved tilt mechanism capable of handling a heavy load on the patient positioning platform would be highly desirable.

Additionally, space in an operating room is at a premium with added equipment, a patient positioning platform, and room for a doctor to operate and move around the patient. Therefore, a patient positioning platform and tilt mechanism that are compact in size would be highly desirable. Furthermore, a tilt mechanism that is easily usable would be highly desirable.

Thus, a need exists for an improved method and apparatus for tilting in a patient positioning platform.

BRIEF SUMMARY OF THE INVENTION

Certain embodiments include a system and method for tilting the patient positioning system. The system includes a patient positioning surface for supporting a patient, a lift subsystem for adjusting elevation of the patient positioning surface, a longitudinal subsystem for moving the patient positioning surface in a longitudinal direction, and a tilt subsystem for tilting the patient positioning surface. The tilt subsystem is capable of tilting the patient positioning surface in a longitudinal direction while supporting a patient load. The system also includes a position sensor for determining a position of the patient positioning surface, and a control subsystem for controlling operation of the patient positioning system.

The system may also include a lateral subsystem for moving the patient positioning surface in a lateral direction, and a rotation subsystem for rotating the patient positioning surface. The system may further include at least one brake to halt motion of the patient positioning surface. In an embodiment, the position sensor includes at least one encoder capable of triggering the brake(s).

Additionally, the tilt system may include a motor, a nut, and a screw. The motor turns the nut. The nut is situated on a screw. The nut translates rotary motion from the motor to linear motion. The screw moves a tilt plate using linear motion from the nut. The system may further include a drive gear situated on the motor, a driven gear situated on the nut that meshes with the drive gear, and a brake gear that meshes with the driven gear.

The method includes tilting the patient positioning surface in a longitudinal direction to position the patient positioning surface for a medical procedure. The method may also include maintaining a region of interest of the patient during movement of the patient positioning surface. The method may further include tilting the patient positioning surface for imaging in an imaging area. Additionally, the method may include rotating or vertically positioning the patient positioning surface to a desired position.

Furthermore, the method may include returning the patient platform to a horizontal position for an emergency situation. The method may also include locking the patient positioning surface. Additionally, the method may include manually moving the patient positioning surface in a longitudinal direction. Also, the method may include halting motion of the patient positioning surface if a clearance distance between the patient positioning surface and an object is less than or equal to a minimum safe clearance distance.

In an embodiment, a tilt mechanism for tilting a patient positioning surface includes a tilt plate for tilting a patient positioning surface, a screw for moving the tilt plate, a nut for translating rotary motion into linear motion to drive the screw, and a motor for imparting rotary motion to the nut. In an embodiment, the screw is a ball screw. In an embodiment, the nut is a rotary nut.

The mechanism may also include a drive gear situated on the motor, a driven gear situated on the nut that meshes with the drive gear, and a brake gear that meshes with the driven gear. The mechanism may also include a fail-safe brake preventing collapse of the tilt mechanism in the event of a component failure.

BRIEF DESCRIPTION OF SEVERAL VIEWS OF THE DRAWINGS

FIG. 7 shows a flow diagram for a method of tilting a patient positioning surface in accordance with an embodiment of the present invention.

Figure 1A:
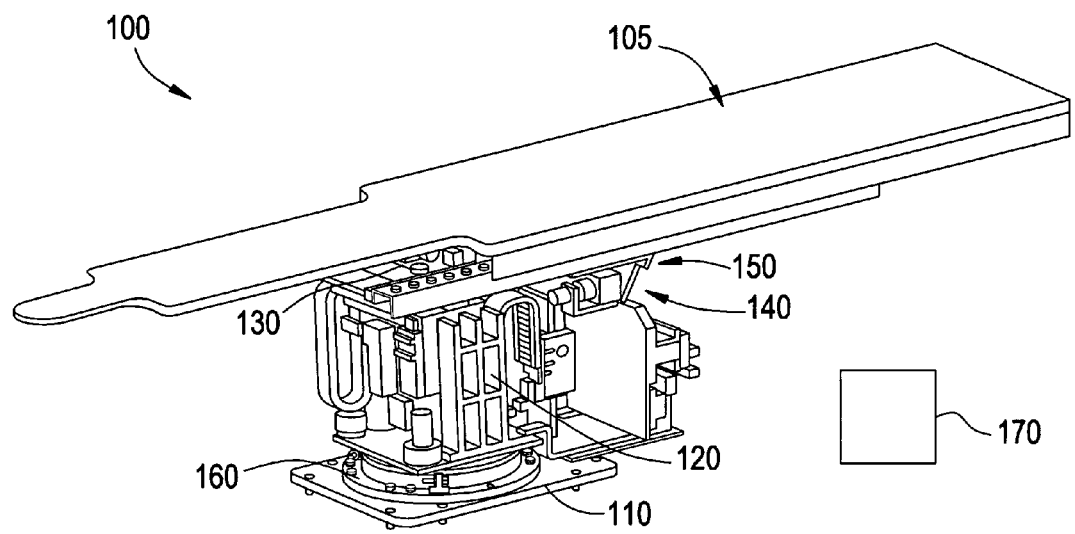
FIGS. 1A and 1B illustrate a patient positioning system that is used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1B:
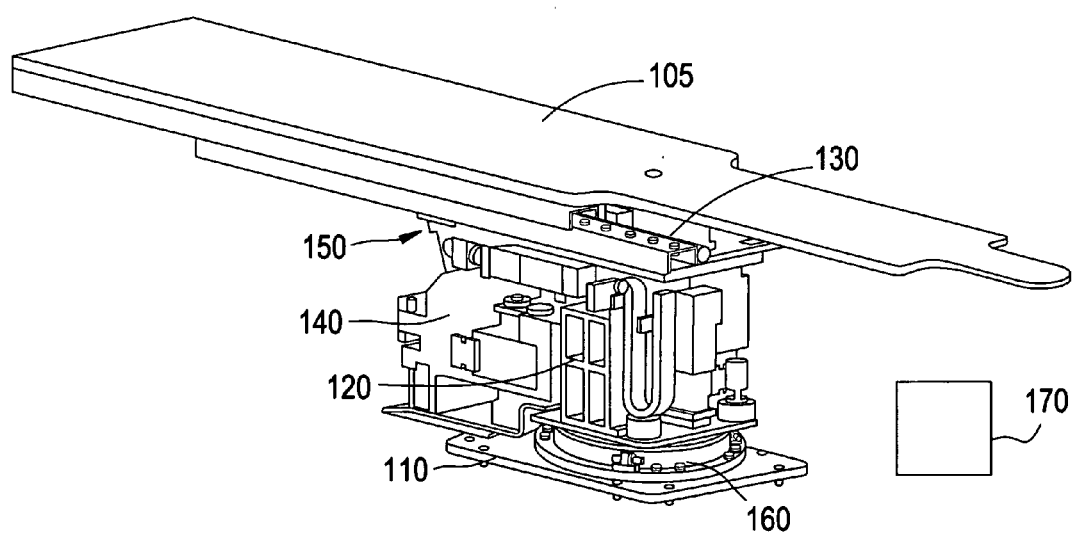
Figure 2A:
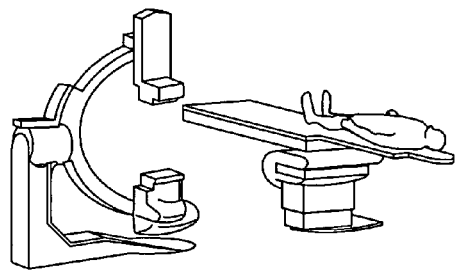
FIGS. 2A, 2B, 2C and 2D illustrate positions of a patient positioning surface used in accordance with an embodiment of the present invention.
Figure 2B:
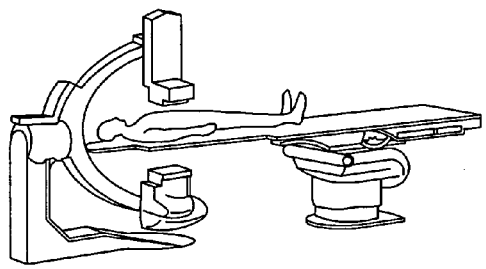
Figure 2C:
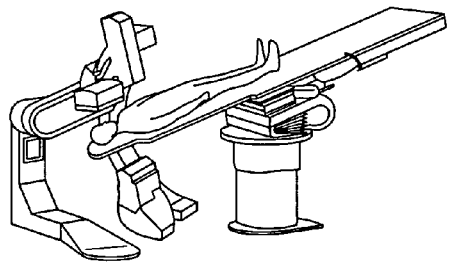
Figure 2D:
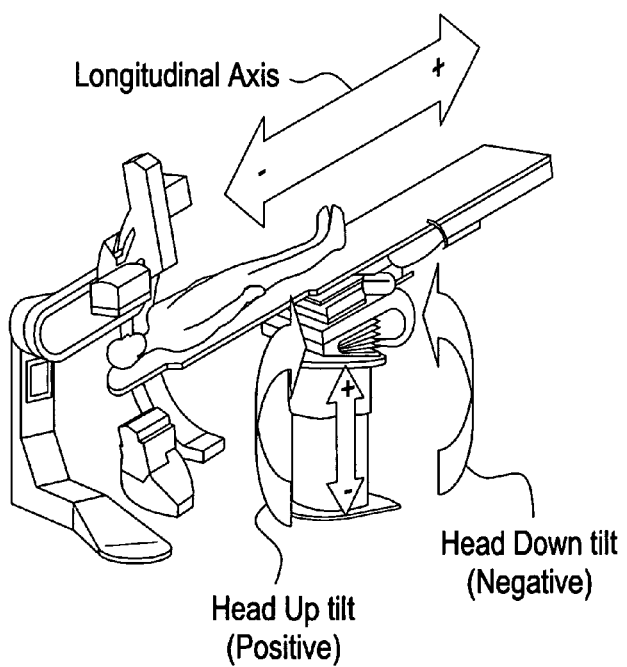
Figure 3A:
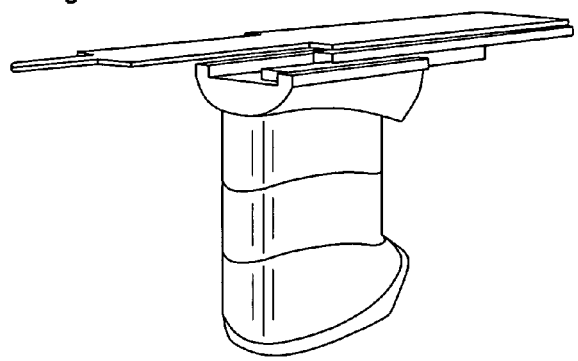
FIGS. 3A, 3B, 3C and 3D illustrate positions of a patient positioning surface used in accordance with an embodiment of the present invention.
Figure 3B:
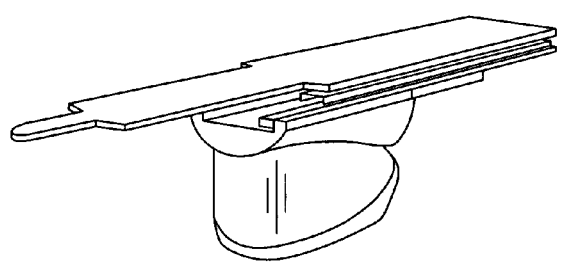
Figure 3C:
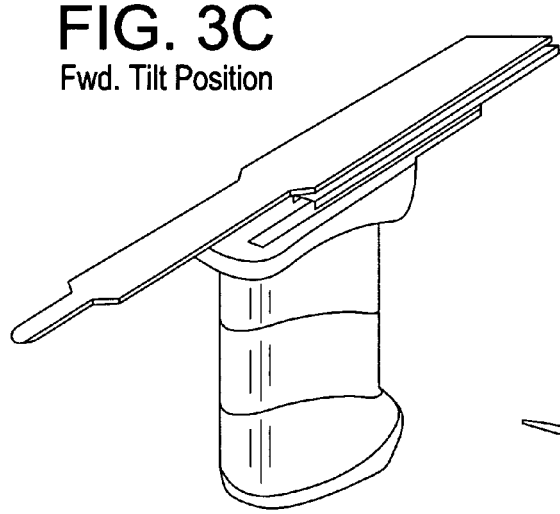
Figure 3D:
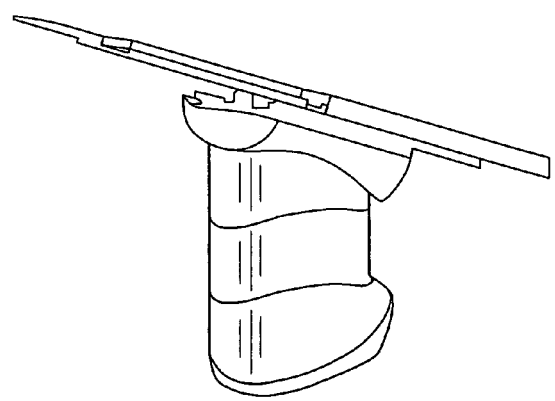

FIGS. 1A and 1B illustrate a patient positioning system 100 that is used in accordance with an embodiment of the present invention. The patient positioning system 100 includes a patient positioning surface 105, a base 110, a telescopic lift system 120, a longitudinal system 130, a tilt system 140, a lateral system 150 and a rotation system 160. The patient positioning system 100 is grouted, or fixed to the floor at the table base 110. The system 100 also includes a motion control system 170. The patient positioning system is described in more detail in U.S. patent application entitled "Grouted Tilting Patient Positioning Table for Vascular Applications," application Ser. No. 10/065,866, filed on Nov. 26, 2002, with inventors Muthuvelan Varadharajulu, Rajagopal Narayanasamy, Baskar Somasundaram, and Shaji Alakkat. The application is herein incorporated by reference including the specification, drawings, claims, abstract, and the like. Additionally, the following U.S. patent applications are also incorporated by reference: "Method and Apparatus for Collision Avoidance in a Patient Positioning Platform," application Ser. No. 10/248,759, filed on Feb. 25, 2003, with inventor Muthuvelan Varadharajulu; "Synchronization Drive for a Longitudinal Axis Telescopic Guidance Mechanism," Ser. No. 10/379,138, filed on Mar. 4, 2003, with inventor Baskar Somasundaram; and "Multiconfiguration Braking System," Ser. No. 10/379,122, filed on Mar. 4, 2003, with inventor Baskar Somasundaram.

To enhance loading and unloading of a patient, the patient positioning surface 105 may rotate around a vertical axis using the rotation system 160. The patient positioning surface 105 may also be manually rotated about the rotation system 160. To move the patient to an image area, the patient positioning surface 105 may move vertically using the telescopic lift system 120 from a height at which the patient may be conveniently loaded to a height where imaging may occur (780 mm to 1080 mm, for example). To move a portion of the patient's body into the image area, the patient positioning surface 105 may move in a lateral direction (+/−140 mm from a normal imaging position, for example) using the lateral system 150. FIGS. 2A, 2B, 2C, 2D, 3A, 3B, 3D and 3D illustrate exemplary positions of the patient positioning surface 105 used in accordance with certain embodiments of the present invention.

Figure 4A:
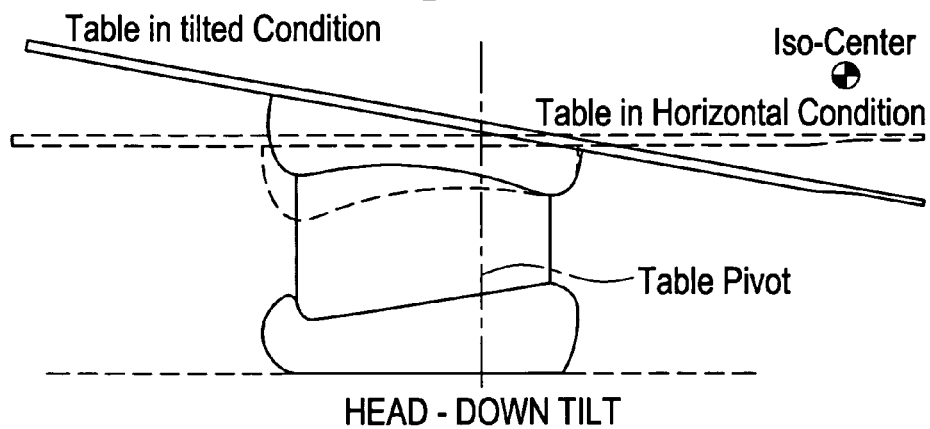
FIGS. 4A, 4B and 4C depict a tilting of a patient positioning surface with and without iso-center tracking used in accordance with an embodiment of the present invention.
Figure 4B:
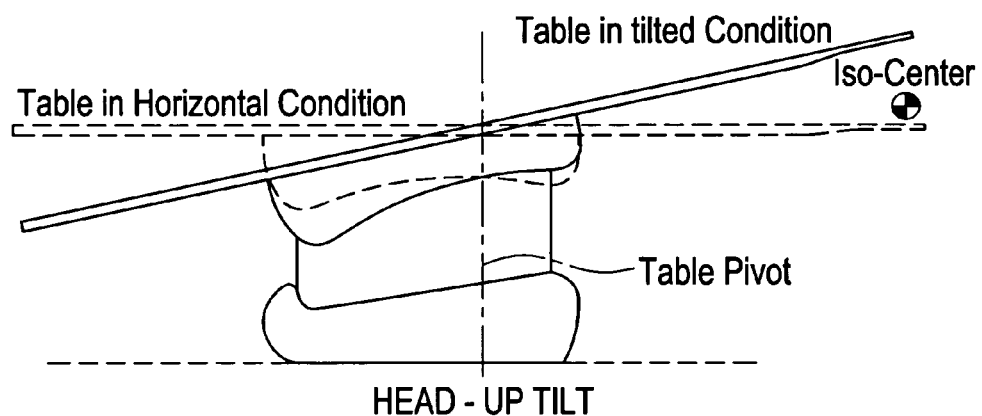
Figure 4C:
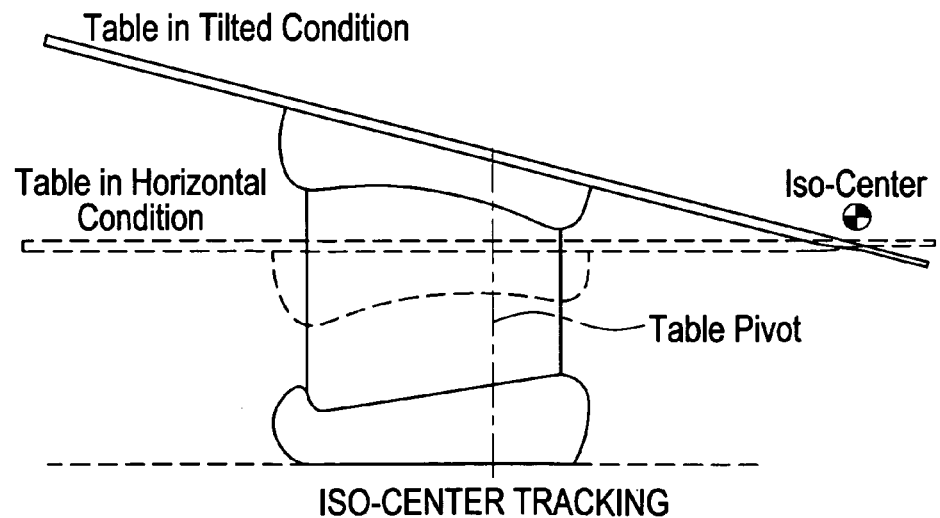

Additionally, the telescopic lift system 120 may provide a stroke or lift motion for iso-center tracking. Iso-center is the point at which three axes of an x-ray imaging system gantry meet (not shown). Iso-center tracking maintains a patient region of interest at the iso-center during tilt or other movement of the patient positioning system 100. Additional stroke for iso-center tracking is provided by the telescopic lift system 120 supported by a telescopic guide mechanism to accommodate a moment resulting from overhanging load. FIGS. 4A, 4B and 4C depict a tilting of the patient positioning surface 105 with and without iso-center tracking used in accordance with an embodiment of the present invention.

For head to toe coverage of the patient, the patient positioning system 100 may use longitudinal motion from the longitudinal system 130. For bolus chasing (following a bolus or contrast agent through a patient's blood vessels), the longitudinal motion may be motorized with a variable speed motor (2 to 15 cm/sec, for example) using the longitudinal system 130 and a guide mechanism. In a certain embodiment, in addition to motorized motion, lateral and longitudinal axes include a clutch to support manual panning of the patient positioning surface 105. That is, the clutch may be released to allow the patient positioning surface 105 to be positioned manually by an operator.

For emerging vascular procedures, such as emergent situations (falling artery pressure, for example), venous access and $CO_2$ studies, the patient positioning surface 105 may tilt head up and head down in the longitudinal direction (12 degrees up and 20 degrees down, for example). A region of interest of the patient may remain at the iso-center or the image area when the patient positioning surface 105 is tilted. In an embodiment, the region of interest remains in the iso-center or the image area using synchronized motion of the telescopic lift system 120, the longitudinal system 130 and the tilt system 140 as defined by the Inverse Kinematics Formula.

In an embodiment, mechanical and electrical interlocks and position feedback from the patient positioning system 100 help to ensure patient safety. Patient restraints may be provided to keep the patient on the patient positioning surface 105 and to help ensure patient safety. Certain embodiments of the patient positioning system 100 help to ensure a high level of patient safety through effective safety interlock systems and redundant systems for avoiding single point failures.

Safety interlocks and redundant safety systems are provided to help ensure patient safety in the patient positioning system 100. In an embodiment, all axes in the patient positioning system 100 are designed to have position encoders to read the coordinates of the patient positioning surface 105 at any position at any time. Ground clearance of the patient positioning surface 105 is calculated, and motion of the patient positioning surface 105 stops if the ground clearance is less than or equal to a specified safe limit. Thus, collisions may be avoided.

In a certain embodiment, all axes are designed with redundant safety systems to avoid single point failures and to help ensure patient safety. Each motorized axis of the patient positioning system 100 may include an incremental encoder and brake (on the drive or motor side). Each motorized axis may also include an absolute encoder and brake at the load side. During normal operation, the brake at the drive side operates to stop any axis of motion. If a problem arises in the driveline, a difference in incremental encoder (drive side) and absolute encoder (load side) readings operates the brake at the load side to stop the axis. Additionally, both power-on and power-off brakes may be activated during procedures to ensure stability and rigidity of the patient positioning surface 105. During power-off conditions, only the power-off brake may be activated to allow easy removal of the patient by rotating the patient positioning surface 105.

The patient positioning surface 105 may be prevented from tilting at the lowest position of the patient positioning surface 105, since the lowest position of the patient positioning surface 105 is used for easy loading and unloading of the patient. Each axis is provided with a power-off brake to lock the motion during a power failure and/or any malfunction of the motors and servo drives. Each axis is provided with a software limit, a hardware limit, and mechanical hard stops. An example of a software limit is the following: during normal operations, the patient positioning surface 105 shall not move beyond a certain point. An example of a hard limit is the following: the patient positioning surface 105 is controlled by a limit switch. The limit switch stops the motion of the patient positioning surface 105 if a software malfunction occurs. An example of a mechanical hard stop is as follows: an end stop is provided as backup if both software and hardware limits fail. The coordinates of all axes may be continuously monitored to avoid a collision with the ground and/or predetermined objects.

The following are some examples of operations involving the patient positioning system 100. The examples are provided to illustrate use of components and systems in the patient positioning system 100 and are not intended to be a comprehensive list.

For example, a patient may be loaded on the patient positioning surface 105. First, the patient positioning surface 105 is positioned at 780 mm from the ground using the telescopic lift system 120. Then, the patient positioning surface 105 is rotated to the right-hand or left-hand side using the rotation system 160. Next, the patient is loaded onto the patient positioning surface 105. Patient restraints may be used to secure the patient on the patient positioning surface 105. To unload the patient, the patient positioning surface 105 is rotated to the right-hand or left-hand side using the rotation system 160. The patient positioning surface 105 is repositioned to a height of 780 mm from ground level by the lift system 120. The patient restraints are unlocked, and the patient is removed from the patient positioning surface 105.

Also, for example, the patient may be moved into the image area. First, the rotation system 160 rotates the patient positioning surface 105 to zero degree. Next, the patient positioning surface 105 is moved vertically to the image area using the telescopic lift system 120. Then, the patient positioning surface 105 is adjusted laterally in the image area with the lateral system 150. The patient positioning surface 105 may also be adjusted longitudinally by the longitudinal system 130 to reach a desired position in the image area.

A patient may be positioned on the patient positioning surface 105 for several medical procedures and examinations. For example, in angiography, a patient's height may be adjusted by raising and lowering the patient positioning surface 105 using the telescopic lift system 120. Additionally, four-way panning may be accomplished using the lateral system 150 and the longitudinal system 130. For peripheral angiography, the patient positioning surface 105 may also be rotated into proper position using the rotation system 160 and tilted using the tilt system 140.

For bolus chasing, patient restraints may be used to secure the patient on the patient positioning surface 105. The longitudinal system 130 advances the patient positioning surface 105 in the longitudinal direction in bolus mode (0–15 cm/sec). For venous access and $CO_2$ studies, for example, patient restraints may keep the patient in touch with the patient positioning surface 105, and the lift 120, longitudinal 130, and tilt 140 systems may be used for iso-center tracking to maintain a desired image area during movement. In emergent situations, restraints secure the patient on the patient positioning surface 105, and the tilt system 140 tilts the patient to a desired position.

Cardiac pulmonary resuscitation (CPR) is a procedure performed for patients who suffer from cardiac arrest, for example. In order to bring a patient to a CPR position if the patient positioning surface 105 is in a horizontal position, the patient positioning surface 105 is moved longitudinally in a backward direction using the longitudinal system 130. Then, the patient positioning surface 105 is lowered using the lift system 120. If the patient positioning surface 105 is titled, the tilt system 140 returns the patient positioning surface 105 to a horizontal position. Then, the longitudinal system 130 moves the patient positioning surface 105 backward, and the lift system 120 lowers the patient positioning surface 105 to enable CPR to be performed on the patient.

The telescopic lift system 120 is used by the patient positioning system 100 to accommodate high load, moments, and lift motion or stroke to position a patient in the image area. The tilt system 140 allows the patient positioning system 100 to tilt head up or head down and maintain a desired image through iso-center tracking. The patient positioning system 100 includes a lateral system 150 to move the patient positioning surface 105 laterally using motorized and/or manual panning.

The patient positioning system 100 supports motorized bolus chasing with head to toe coverage so that an image may be traced as the contrast agent travels through the patient. The patient positioning system 100 tracks the coordinates of the patient positioning surface 105. Positioning tracking facilitates collision avoidance with the ground and/or other predetermined objects. Tracking also allows the patient positioning system 100 to return the patient positioning surface 105 to a previously recorded and/or memorized position.

Examples of complex motion of the patient positioning system 100 have been described above. Execution of complex motions to position the patient positioning surface 105 for various medical procedures creates a risk of collision between the patient positioning surface 105 and the ground and/or another object in the examination room. Certain embodiments of the present invention provide a system and method for collision avoidance.

The motion control system 170 for the patient positioning system 100 includes three major parts: a user interface, an I/O board, and servo nodes (not shown). A user may move the patient positioning surface 105 using the user interface. User interface commands are processed by the I/O board (CPU). Commands are then sent to corresponding servo nodes that control the respective axis movements. In an embodiment, a Power PC-based micro controller is used as the CPU. An application program, which is running on a real-time operating system, may control the patient positioning system 100.

Clearance between the patient positioning surface 105 and the ground and/or another object is determined dynamically based on the positions of the lift, longitudinal, and tilt axes in the patient positioning system 100. The motion control system 170 may store a safe clearance value. The motion control system 170 determines the clearance between the patient positioning surface 105 and the ground or another object. The motion control system 170 compares the measured clearance and the safe clearance value. The motion control system 170 stops movement of axes of the patient positioning system 100 if the measured clearance is less than or equal to the stored safe clearance.

Figure 5:
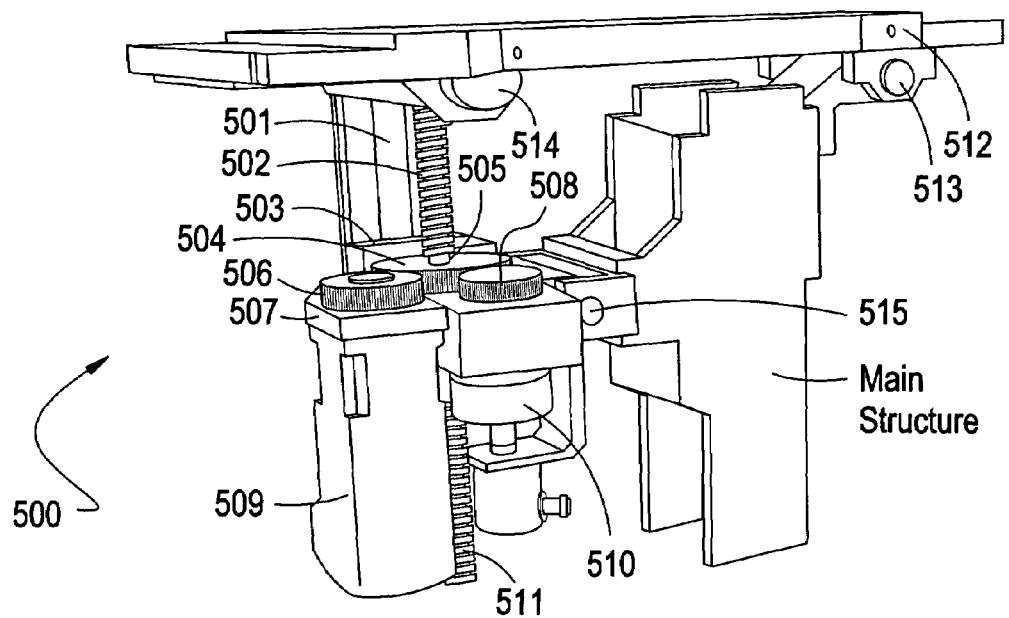
FIG. 5 illustrates a tilt system for a patient positioning system used in accordance with an embodiment of the present invention.
Figure 6A:
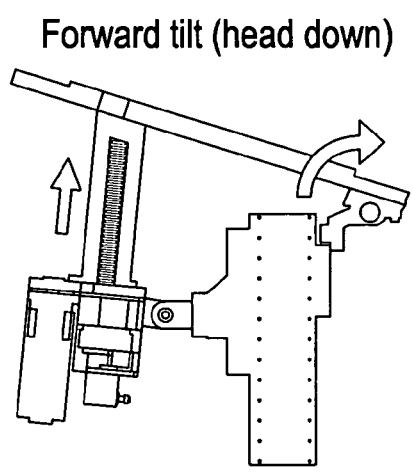
FIGS. 6A, 6B 6C and 6D illustrate tilting a patient positioning surface in a patient positioning system used in accordance with an embodiment of the present invention.
Figure 6B:
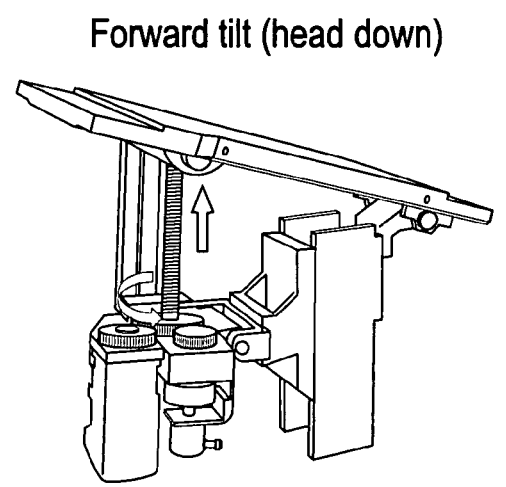
Figure 6C:
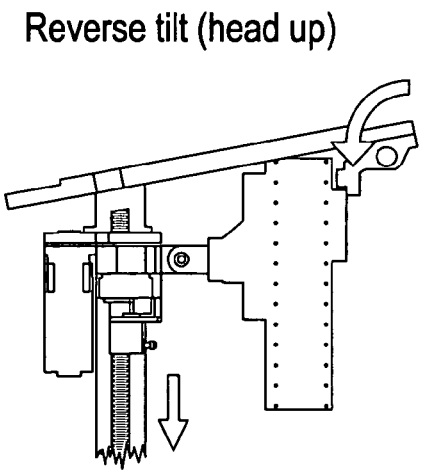
Figure 6D:
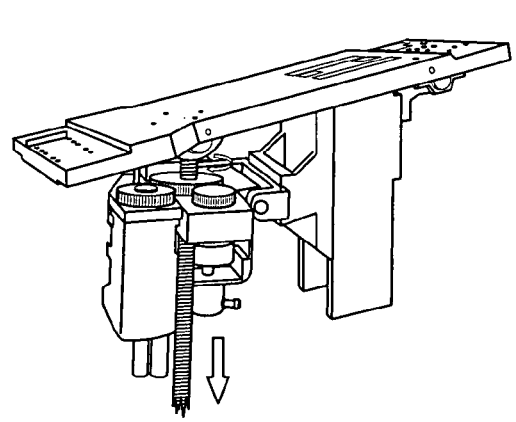

FIG. 5 illustrates a tilt system 500 for a patient positioning system used in accordance with an embodiment of the present invention. The tilt system 500 is similar to the tilt system 140 described above in relation to FIGS. 1A and 1B and the patient positioning system 100. The tilt system 500 is capable of tilting the patient positioning surface 105 head up and head down in the longitudinal direction (+/−20 degrees, for example). The tilt system 500 also supports iso-center tracking during a tilt (head down at 16 degrees, for example). FIGS. 6A, 6B, 6C and 6D illustrate tilting a patient positioning surface 105 in a patient positioning system 100 used in accordance with an embodiment of the present invention.

The tilt system 500 includes a tilt drive system. The tilt drive system includes a ball screw 502 and a rotary nut 505 driven by a motor 509. In an embodiment, the tilt drive system is hinged at the rear side of the patient positioning surface 105. The tilt system 500 includes a LM guide 501 to compensate for moments. In an embodiment, the tilt system 500 is hinged at the front side of the patient positioning surface 105. The motor 509 drives the rotary nut 505. The rotary nut 505 linearly translates the ball screw 502 for tilt about the hinge at the front of the patient positioning surface 105.

The tilt system 500 is fixed to the main structure of the lift system 120. A tilt plate 512 is hinged to the main structure through a hinge 514 of the tilt axis 513 at the front side of the main structure. The tilt plate 512 is supported at the rear by a LM guide 501 and the non-rotating ball screw 502 through the hinge 514. The rotary nut 505 of the ball screw 502 and LM guide blocks 503 are housed on a plate 507 that is mounted to the main structure through a hinge 515. The motor 509 with a brake and an incremental encoder is mounted to the plate 507. A drive gear 506 on the motor 509 meshes with a driven gear 504 on the rotary nut 505 of the ball screw 502. The driven gear 504 also meshes with a brake gear 508. A fail-safe electromagnetic brake 510 and an absolute encoder 511 are mounted on the shaft of the brake gear 508.

The motor 509 drives the rotary nut 505 of the ball screw 502 through the drive gear 506 and the driven gear 504. The rotary nut 505 translates rotary motion into linear motion of the non-rotating ball screw 502 which may push/pull the tilt plate 512 with respect to the tilt axis 513. The driven gear 504 meshes with the brake gear 508. The fail-safe electromagnetic brake 510 is mounted onto the brake gear 508 shaft. The fail-safe brake 510 may prevent the tilt system 500 from collapsing even if the drive gear 506, motor 509, and/or motor brake fails. The fail-safe electromagnetic brake 510 prevents collapse by sensing signals from the incremental encoder in the motor 509 and the absolute encoder 511 connected to the brake gear 508 shaft.

FIG. 7 shows a flow diagram for a method of tilting a patient positioning surface in accordance with an embodiment of the present invention. First, at step 710, the patient positioning surface 105 is positioning vertically at a desired distance from the ground, such as 780 mm. Then, at step 720, the patient is loaded onto the patient positioning surface 105.

At step 730, the patient positioning surface 105 is tilted. The patient positioning surface 105 may be tilted to position the patient or a region of interest in the patient in an image area. Iso-center tracking may be used to maintain the position of a patient region of interest inside the image area. Additionally, the patient positioning surface 105 may be tilted to allow access to the patient by a doctor for a medical procedure. The patient positioning surface 105 may also be rotated to a desired position.

Then, at step 740, the patient positioning surface 105 may be tilted back to a horizontal position. The patient positioning surface 105 may also be rotated to a desired position. Next, at step 750, the patient may be removed from the patient positioning surface 105. Additionally, an emergence procedure, such as CPR, may be performed.

Thus, certain embodiments of the present invention provide a tilt mechanism 500 for a patient positioning system 100 that tilts the patient positioning surface 105 in both directions longitudinally. Additionally, the tilt system 500 is compact and minimally adds to height and width of the patient positioning system 100. The tilt mechanism 500 accommodates a heavy load on the patient positioning surface 105 when the surface 105 is tilted. Certain embodiments of the present invention accommodate a heavy moment load on the tilt mechanism 500 when load is applied away from the tilt mechanism 500.

In certain embodiments, the tilt system 500 uses standard off-the-shelf parts, such as ball screws, rotary nuts, bearings, etc. Loads are distributed through linear motion guides. Axial loads are taken through the ball screw. In certain embodiments, a position accuracy of +/−0.1 mm is maintained. Linear guidance elements and greased ball screws and nuts provide for durability and low maintenance. A fail-safe brake on the load side of the patient positioning surface 105 using encoder feedback helps prevent a collapse of the tilt mechanism 500 even if the drive gear, motor, and/or motor brake fail.

Certain embodiments provide new, simple mechanisms to convert rotary motion into linear motion and, in turn, resulting angular motion. Certain embodiments maintain position accuracy of the patient positioning system 100. Certain embodiments also maintain load carrying capacity of the patient positioning system 100 during forward and reverse tilts. The compact tilt mechanism 500 may be designed with linear motion elements, drive elements, and safety elements. Fail-safe brakes may be included for patient safety.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A patient positioning system for medical applications, said system comprising:
   a patient positioning surface for supporting a patient;
   a lift subsystem for adjusting elevation of said patient positioning surface;

a longitudinal subsystem including a motor for moving said patient positioning surface in a longitudinal direction;

a tilt subsystem for tilting said patient positioning surface, said tilt subsystem capable of tilting said patient positioning surface in a longitudinal direction while supporting a patient load;

a position sensor for determining a position of said patient positioning surface;

at least one brake configured to stop motion of said patient positioning surface when power is removed from said brake; and a control subsystem for controlling operation of said patient positioning system.

2. The system of claim 1, further comprising a lateral subsystem for moving said patient positioning surface in a lateral direction.

3. The system of claim 1, further comprising a rotation subsystem for rotating said patient positioning surface.

4. The system of claim 1, further comprising at least one brake to halt motion of said patient positioning surface.

5. The system of claim 4, wherein said position sensor comprises at least one encoder capable of triggering said at least one brake.

6. A patient positioning system for medical applications, said system comprising:

a patient positioning surface for supporting a patient;

a lift subsystem for adjusting elevation of said patient positioning surface;

a longitudinal subsystem for moving said patient positioning surface in a longitudinal direction;

a tilt subsystem for tilting said patient positioning surface, said tilt subsystem capable of tilting said patient positioning surface in a longitudinal direction while supporting a patient load;

a position sensor for determining a position of said patient positioning surface; and a control subsystem for controlling operation of said patient positioning system, wherein said tilt subsystem further comprises:
   a motor for turning a nut;
   a nut configured to translate rotary motion from said motor to linear motion; and
   a screw for moving a tilt plate using linear motion from said nut, wherein said nut is situated on said screw.

7. A patient positioning system for medical applications, said system comprising:

a patient positioning surface for supporting a patient;

a lift subsystem for adjusting elevation of said patient positioning surface;

a longitudinal subsystem for moving said patient positioning surface in a longitudinal direction;

a tilt subsystem for tilting said patient positioning surface, said tilt subsystem capable of tilting said patient positioning surface in a longitudinal direction while supporting a patient load;

a position sensor for determining a position of said patient positioning surface;

a control subsystem for controlling operation of said patient positioning system;

a drive gear situated on said motor;

a driven gear situated on said nut, said driven gear meshing with said drive gear; and a brake gear, said brake gear meshing with said driven gear, wherein said tilt subsystem further comprises:
   a motor for turning a nut;
   a nut configured to translate rotary motion from said motor to linear motion; and
   a screw for moving a tilt plate using linear motion from said nut, wherein said nut is situated on said screw.

8. A tilt mechanism for tilting a patient positioning surface, said mechanism comprising:

a tilt plate for tilting a patient positioning surface in a longitudinal direction;

a screw for moving said tilt plate;

a nut for translating rotary motion into linear motion to linearly drive said screw;

a motor for imparting rotary motion to said nut; and an electromagnetic brake connected to said motor by at least one gear.

9. The mechanism of claim 8, wherein said screw comprises a ball screw.

10. The mechanism of claim 8, wherein said nut comprises a rotary nut.

11. A tilt mechanism for tilting a patient positioning surface, said mechanism comprising:

a tilt plate for tilting a patient positioning surface;

a screw for moving said tilt plate;

a nut for translating rotary motion into linear motion to drive said screw;

a motor for imparting rotary motion to said nut;

a drive gear situated on said motor;

a driven gear situated on said nut, said driven gear meshing with said drive gear; and a brake gear, said brake gear meshing with said driven gear.

12. A method for tilting a patient positioning surface, said method comprising:

vertically positioning a patient surface at a desired height to allow a patient to be loaded onto said patient positioning surface;

tilting said patient positioning surface in a longitudinal direction to position said patient positioning surface for a medical procedure;

returning said patient positioning surface to a horizontal position for an emergency situation; and locking said patient surface using at least one electromagnetic brake.

13. A method for tilting a patient positioning surface, said method comprising:

vertically positioning a patient surface at a desired height to allow a patient to be loaded onto said patient positioning surface;

tilting said patient positioning surface in a longitudinal direction to position said patient positioning surface for a medical procedure; and locking said patient positioning surface using at least one electromagnetic brake.

* * * * *